US00PP19902P3

(12) United States Plant Patent
Danziger

(10) Patent No.: US PP19,902 P3
(45) Date of Patent: Apr. 14, 2009

(54) ***TORENIA* PLANT NAMED 'DANMOON 18'**

(50) Latin Name: ***Torenia* sp.**
Varietal Denomination: DANMOON18

(75) Inventor: Gabriel Danziger, Moshav Nir-Zvi (IL)

(73) Assignee: Danziger "Dan" Flower Farm, Post Beit Dagan (IL)

( * ) Notice: Subject to any disclaimer, the term of this patent is extended or adjusted under 35 U.S.C. 154(b) by 279 days.

(21) Appl. No.: 11/544,753

(22) Filed: Oct. 10, 2006

(65) Prior Publication Data

US 2008/0134386 P1 Jun. 5, 2008

(51) Int. Cl.
*A01H 5/00* (2006.01)

(52) U.S. Cl. ..... Plt./487

(58) Field of Classification Search ..... Plt./487
See application file for complete search history.

*Primary Examiner*—Kent L Bell
(74) *Attorney, Agent, or Firm*—Foley & Lardner LLP

(57) ABSTRACT

A new and distinct *Torenia* plant named 'DANMOON18' particularly characterized by plenty of delicate, funnel form, cup-shaped flowers with petals in a combination of purple, violet and gray shades with a yellow blotch on the lower petal; trailing bush habit; vigorous growth habit; densely branched plant, gracefully cascading from hanging baskets; early flowering response and stays in full bloom in moderate climate; suitable as an annual for hanging pots outdoors under partial shade; and good weather tolerance with a preferred temperature range of 15° C. to 25° C.

2 Drawing Sheets

Latin name of the genus and species of the plant claimed: *Torenia* sp.
Variety denomination: 'DANMOON18'.

BACKGROUND OF THE INVENTION

The present invention relates to a new and distinct cultivar of *Torenia* plant, botanically known as *Torenia* sp. of the *Scrophulariaceae* family, and hereinafter referred to by the cultivar name 'DANMOON18'.

The new *Torenia* cultivar is a product of a controlled breeding program conducted by the inventor, Gabriel Danziger, in Moshav Mishmar Hashiva, Israel. The objective of the breeding program was to develop a new *Torenia* cultivar with purple and gray flowers.

The new *Torenia* cultivar originated from an induced mutation of the *Torenia* cultivar designated 'TR-3-1202' (unpatented). The new *Torenia* cultivar was discovered and selected by the inventor, Gabriel Danziger, as a single flowering plant within the progeny of the stated mutation in a controlled environment in January of 2005 in Moshav Mishmar Hashiva, Israel.

Asexual reproduction of the new *Torenia* cultivar by soft tip cuttings was first performed in June of 2005 in Moshav Mishmar Hashiva, Israel, and has demonstrated that the combination of characteristics as herein disclosed for the new cultivar are firmly fixed and retained through successive generations of asexual reproduction. The new cultivar reproduces true to type.

BRIEF DESCRIPTION OF THE INVENTION

The following traits have been repeatedly observed and are determined to be basic characteristics of 'DANMOON18' which in combination distinguish this *Torenia* as a new and distinct cultivar:

1. Plenty of delicate, funnel form, cup-shaped flowers with petals in a combination of purple, violet and gray shades with a yellow blotch on the lower petal;
2. Trailing bush habit;
3. Vigorous growth habit;
4. Densely branched plant, gracefully cascading from hanging baskets;
5. Early flowering response and stays in full bloom in moderate climate;
6. Suitable as an annual for hanging pots outdoors under partial shade; and
7. Good weather tolerance with a preferred temperature range of 15° C. to 25° C.

Plants of the new *Torenia* cultivar 'DANMOON18' differ from 'TR-3-1202' in the following characteristics described in Table I.

TABLE 1

| Characteristic | New Cultivar 'DANMOON18' | Parent 'TR-3-1202' (unpatented) |
|---|---|---|
| Mature Flower color | Petal shades of purple, violet and gray, with a yellow blotch on lower petal | Petal shades of violet, with a yellow blotch on lower petal |
| Flower size | Depth: About 4.0 cm<br>Width: About 3.2 cm | Depth: About 3.0 cm<br>Width: About 3.0 cm |
| Growth habit | Trailing Bush | Cascading Bush |
| Flowering Response Time | 3 weeks from planting | 3 weeks from planting |

Of the many commercial cultivars known to the present inventor, the most similar in comparison to the new *Torenia* cultivar 'DANMOON18' is the *Torenia* cultivar 'ROSE MOON' (unpatented) in the following characteristics described in Table 2:

TABLE 2

| Characteristic | New Cultivar 'DANMOON18' | Comparison Cultivar 'ROSE MOON' (unpatented) |
|---|---|---|
| Mature Flower Color | Petal shades of purple, violet and gray, with a yellow blotch on lower petal | Petal shades of light red-purple, with a yellow blotch on lower petal |
| Flower Size | Depth: About 4.0 cm Width: About 3.2 cm | Depth: About 3.5 cm Width: About 3.8 cm |
| Growth Habit | Trailing Bush | Cascading Bush |
| Flowering Response Time | 3 weeks from planting | 7 weeks from planting |

BRIEF DESCRIPTION OF THE PHOTOGRAPHS

The accompanying photographs illustrate the overall appearance of the new *Torenia* cultivar 'DANMOON18' showing the colors as true as is reasonably possible with colored reproductions of this type. Colors in the photographs may differ slightly from the color values cited in the detailed botanical description, which accurately describe the color of 'DANMOON18'.

DETAILED BOTANICAL DESCRIPTION

Figure 1:
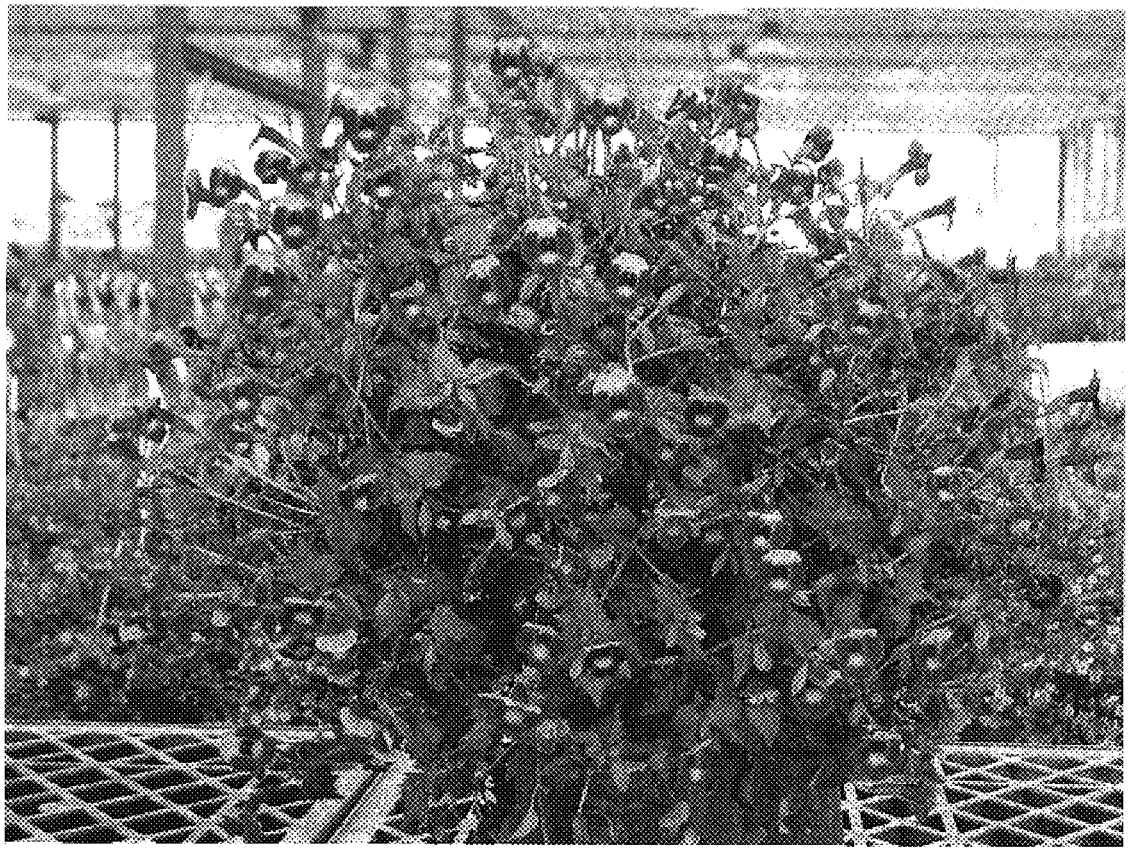
FIG. 1 shows a side perspective view of a typical flowering plant of 'DANMOON18' in a planter at 3 months of age. 'DANMOON18' is the plant pictured in the forefront FIG. 1.
Figure 2:
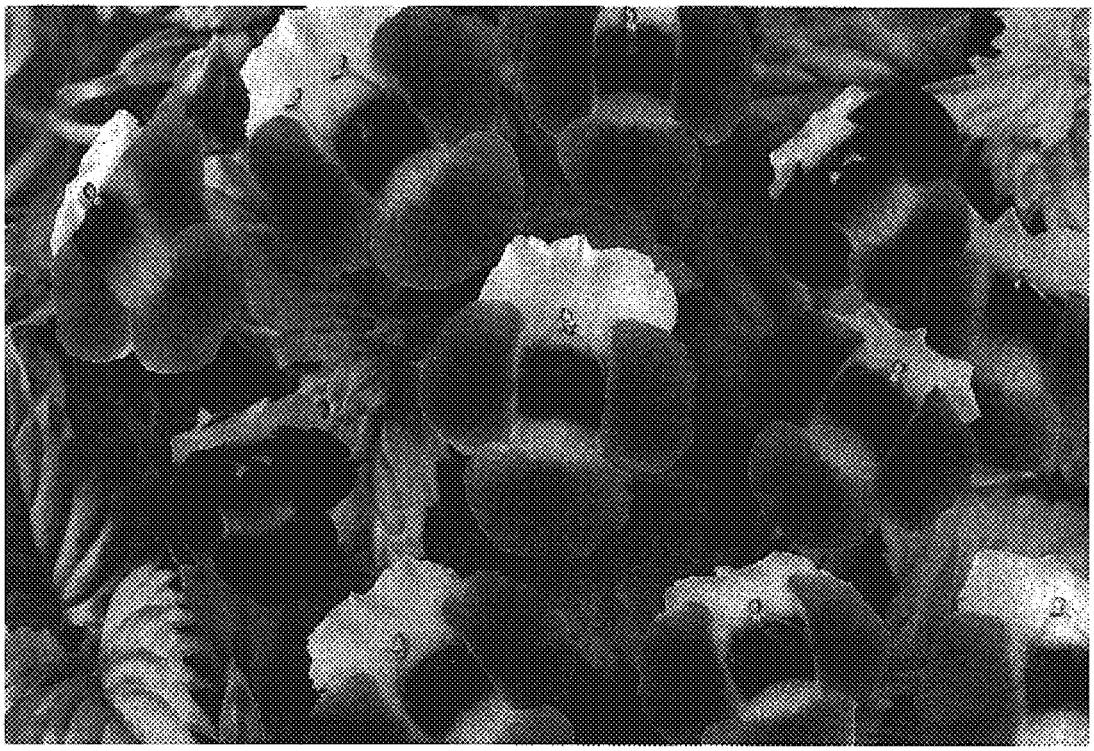
FIG. 2 shows a close-up of the typical flowers, buds and leaves of 'DANMOON18' at 3 months of age.

The new *Torenia* cultivar 'DANMOON18' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'DANMOON18' as grown in a greenhouse in Moshav Mishmar Hashiva, Israel, under conditions which closely approximate those generally used in commercial practice. Optimal growth conditions include that plants of 'DANMOON18' are grown outdoors in a moderate climate and indoors during the winter season. Irrigation and fertilization are recommended on a regular basis. Plants of 'DANMOON18' are usually grown in full sunlight, but partial shade is required in mid summer. Plants of 'DANMOON18' are fully-grown in 2.5 months from planting a cutting in the summer season and bloom all year-round in a moderate climate. The 'DANMOON18' plants described herein were grown indoors in 16 cm pots in a glass greenhouse in Moshav Mishmar Hashiva, Israel, at a day temperatures ranging from 18° C. to 35° C. and night temperatures ranging from 16° C. to 25° C. Plants of 'DANMOON18' were fertilized up to a level of 59 ppm N, 35.4 ppm P and 94.4 ppm K.

Color references are made to the Royal Horticultural Society Colour Chart (R.H.S.), 2001 edition, except where general colors of ordinary significance are used. Color values were taken under daylight conditions at approximately noon in Moshav Mishmar Hashiva, Israel. The age of the 'DANMOON18' plants described is 10 weeks.

Parentage: *Torenia* cultivar designated 'TR-3-1202' (unpatented).

Propagation: Tissue culture and soft tip cuttings.

Plant:

*Form.*—Bush, cascading.

*Growth habit.*—Trailing.

*Height.*—15 to 20 cm.

*Spread.*—About 70 cm.

*Cold tolerance.*—Frost tender. Temperatures below 8° C. may damage plants.

*Vigor.*—Vigorous growth; plants are fully-grown in 2.5 months from planting cuttings during summer season.

Stem:

*Color.*—RHS 144A, yellow-green.

*Length.*—About 25 cm.

*Diameter.*—About 3 mm.

*Pubescence.*—Minimal.

*Branching.*—About 15 to 30 main branches grow from the base and split into hundreds of secondary and tertiary branches.

*Length of internodes.*—1.5 to 14 cm.

Foliage:

*Overall shape.*—Deltoid.

*Apex.*—Acute.

*Base.*—Reniform.

*Size of leaf.*—Width: 2.0 to 4.0 cm. Length: About 4.2 cm.

*Color.*—Center color of leaf: RHS 137A, green. Upper side: RHS 137A, green. Under side: RHS 137B, green.

*Margin.*—Serrate.

*Leaf texture.*—Glabrous with sensible veins.

*Venation.*—Pattern: Anastomotic. Color: Upper surface: RHS 137C, green. Lower surface: RHS 147A, yellow-green.

*Petioles.*—Length: About 0.2 to 1.5 cm. Diameter: About 2.0 mm. Color: RHS 143C, green.

Flowers:

*Blooming period.*—All year round in a moderate climate or in a greenhouse environment. In Israel, flowering occurs between February and November outdoors.

*Flowering response time.*—About 3 weeks from planting.

*Flowering stem.*—Flowers appear along the growing stems.

*Quantity of flowers.*—Per stem: About 4 to 7; Per plant: About 200 to 350.

*Flowering longevity.*—On the plant: About 2 to 5 days, depending on temperature.

*Type.*—Single.

*Shape.*—Overall: funnel form; 5-winged; Corolla tube: cylindrical or often broadened above; Corolla: 2-lipped, the upper lip faintly 2-lobed, the lower lip 3-lobed.

*Orientation at opening.*—Slanted upward.

*Fragrance.*—None.

*Flower size.*—Depth: About 4.0 cm. Width: About 3.2 cm.

*Buds.*—Shape: Oblong, cylindrical, ellipsoid, 5-winged. Size: Length: About 1.8 mm. Diameter: About 0.9 mm. Color: Apex: RHS 146A, yellow-green. Base: RHS 144A, yellow-green. Texture: Pubescence on winged edges.

*Floral tube.*—Length: About 3.2 cm. Width: About 0.3 cm to 1.2 cm. Color: (color changes between upper side of flower tube to the lower one). Outside: Violet shades of RHS 86A (upper side), RHS 83A (middle), and RHS 85A (lower side); Inside: Purple shades of RHS 79B (apex) and RHS N77B (base).

*Petals.*—Number: Four, fused. Length: Upper Petal: About 1.4 cm; Side Petals: About 1.0 cm; Lower Petal: About 1.6 cm. Width: Upper Petal: About 2.2 cm; Side Petals: About 1.2 cm; Lower Petal: About 1.8 cm. Shape: Upper Petal: Overall: spatulate, Apex: rounded, Base: fused; Side Petals: Overall: spatulate, Apex: rounded, Base: fused; Lower: Overall: spatulate, Apex: rounded, Base: fused. Margin: Undulated.

*Color.*—

*Mature petals.*—Upper Surface: Upper Petal: Near apex, RHS 97C, violet-blue, and near base, RHS 86A, violet; and margin, RHS 97C, violet-blue; Side Petals: Primarily RHS 83A, violet, and inner margin RHS 92B, violet-blue; Lower Petal: Primarily RHS 83A violet, with RHS 7B, yellow, blotch in the middle near base, and RHS 91A, violet-blue color surrounding blotch and near base, and margin, RHS 83A, violet. Lower Surface: Upper Petal: Near apex and margin, RHS 85A, violet, and near base, a mixture of violet shades RHS 86A and RHS 86C; Side Petals: Primarily RHS 86A, violet, with RHS 8A, yellow, and margin, RHS 86B, violet; Lower Petal: Near apex, a mixture between RHS 8D, yellow, and RHS 91C, violet-blue, and near base and margin, RHS 84A, violet.

*Throat.*—Upper throat: RHS 86A, violet; Lower throat: RHS 85A, violet.

*Immature petals.*—Upper Surface: Upper Petal: Near apex and margin, RHS 160C, greyed-yellow, near base, RHS 86B, violet; Side Petals: Primarily RHS 79A, purple, and inner margin RHS 91 B, violet-blue; Lower Petal: Primarily RHS 83A, violet, with RHS 163C, greyed-orange blotch in the middle near base. Lower Surface: Upper Petal: Near apex and margin, RHS N 187B, greyed-purple, and near base, RHS 79B, purple; Side Petals: Primarily RHS 79B, purple; Lower Petal: Near apex, RHS 160B, greyed-yellow, and near base, RHS N79A, purple, and margin, RHS N79B, purple; Throat: Center of Flower: RHS 83A, violet.

*Sepals.*—Number: 5 Length: About 1.9 cm Width: About 0.6 cm Shape: Two-lobed, 5-winged Apex: Acute Base: Wedge shaped Margin: Undulated. Color: RHS 144A, yellow-green.

*Peduncle.*—Length: About 2.3 to 4.2 cm. Diameter: About 2.0 mm. Color: RHS 146B, yellow-green.

Reproductive organs:

*Androecium.*—Stamen: Number: 2 pairs per flower, fused. Color: RHS 83A, violet, and RHS 155D, white. Anther: Length: About 0.4 cm, upper anther shorter — about 0.3 cm. Width: About 0.1 cm (separate, usually there are two fused). Color: RHS 155D, white. Spur: Present. Filament: Length: About 1.4 cm; lower filaments are shorter about 0.5 cm. Width: About 0.4 mm. Color: RHS N85A, violet. Pollen: Amount: Sparse. Color: RHS N155C, white. Requirements for pollination: Young flowers, vital pollen, and receptive, open stigma.

*Gynoecium.*—Pistil: Number: One per flower. Length: About 2.9 cm. Stigma: Length: About 0.3 cm. Width: About 0.2 cm. Color: RHS 84A, violet. Style: Length: About 2 cm. Color: RHS 84B, violet. Ovary: Number: 1. Length: About 0.3 cm. Width: About 0.2 cm. Color: RHS 143A, green.

Seed/fruit: None.

Pest/disease resistance and/or susceptibility: A standard preventative spray program is sufficient as no susceptibility was observed.

Temperature tolerance: Sensitive to temperatures below 5° C.

I claim:

1. A new and distinct *Torenia* plant named 'DANMOON18', as illustrated and described herein.

* * * * *